(12) United States Patent
Pointek et al.

(10) Patent No.: US 6,428,984 B1
(45) Date of Patent: Aug. 6, 2002

(54) METHOD FOR OBTAINING RECOMBINANT HBSAG

(75) Inventors: Michael Pointek, Essen; Michael Weniger, Duisburg, both of (DE)

(73) Assignee: Rhein Biotech Gesellschaft fur Neue Biotechnologische Porzesse und Produkte mbH (DE)

( * ) Notice: Subject to any disclaimer, the term of this patent is extended or adjusted under 35 U.S.C. 154(b) by 0 days.

(21) Appl. No.: 09/701,197

(22) PCT Filed: Apr. 17, 2000

(86) PCT No.: PCT/EP00/03476

§ 371 (c)(1),
(2), (4) Date: Feb. 8, 2001

(87) PCT Pub. No.: WO00/65065

PCT Pub. Date: Nov. 2, 2000

(30) Foreign Application Priority Data

Apr. 23, 1999 (DE) .......................................... 199 18 619

(51) Int. Cl.$^7$ .......................... C12N 15/09; C12N 1/16; C07H 21/04
(52) U.S. Cl. .................. 435/69.3; 435/69.3; 435/235.1; 435/254.2; 435/254.21; 435/254.22; 435/254.23; 435/320.1; 435/477; 530/350; 536/23.1; 536/23.72
(58) Field of Search .............................. 435/69.3, 235.1, 435/254.2, 254.21, 254.22, 254.23, 320.1, 477; 530/350; 536/23.1, 23.72

(56) References Cited

U.S. PATENT DOCUMENTS 3,983,008 A    9/1976    Shinozaki et al. .......... 195/104

FOREIGN PATENT DOCUMENTS

EP    0337492 A1 *    4/1989    ........... C12P/21/00

OTHER PUBLICATIONS

Pittroff, M., et al., DECHEMA–Biotechnol. Conf.; (1990), 4, Pt. B, 1055–60.
Pittroff, M., et al., DECHEMA–Biotechnol. Conf.; (1992), 5, Pt.B, 697–91.
Luther, H., et al., Acta–Biotechnol.; (1992) , 12, 4, 281–91.
Schütte, H., Biol. Recombinant–Microorg. Anim. Cells; (1991) O holo 34 Meet., 293–305.
Baldwin, C., Biotechnol. Tech.; (1990), 96, 4, 329–34.
Choo., K.B., et al., Biochem. Biophys. Res. Commun.; (1995), 131, 1, 160–66.
Fenton, D.M., et al., Abstr. Ann. Med. Am. Soc. Microbiol. (1984), 84, Meet. 193.
Pitroff et al. "Mechanischer Aufschluß von Mikroorganismen im Verfahrensvergleich zwischen Naßvermahlung und Hochdruck–Homogenisation", Chem. Ing–Tech., 64, No. 10, pp. 950–953 (1992).
Zbigniew A. Janowicz et al., "Simultaneous Expression of the S and L Surface Antigens of Hepatitis B, and Formation of Mixed Particles in the Methylotropic Yeast, *Hansenula polymorpha*", YEAST, VOL. 7:431–443 (1991).
J. Evangelista Dyr et al., "Separation used for purification of recombinant proteins", Journal of Chromatography B. 699, pp. 383–401, (1997).
Gerd Gellissen et al., "Application of yeasts in gene expression studies: a comparison of *Saccharomyces cerevisiae, Hansenula polymorpha* and *Kluyveromyces lactis*", Gene 190, pp. 87–97 (1997).
J. Baratti, et al., "Preparation and Properties of Immobilized Methanol Oxidase", Department of Nutrition and Science, Massachusetts Institute of Technology, Cambridge, Massachusetts, 02139, pp. 333–348, (1977).

* cited by examiner

Primary Examiner—Karen Cochrane Carlson
Assistant Examiner—Chih-Min Kam
(74) Attorney, Agent, or Firm—Finnegan, Henderson, Farabow, Garrett & Dunner, L.L.P.

(57) ABSTRACT

The present invention relates to a method for recovering recombinant HBsAg, wherein recombinant methylotrophic yeast cells which are capable of expressing HBsAg are disrupted using a high pressure homogenizer, and HBsAg is recovered from the cell debris obtained. The inventive method is characterized by a high product yield per g of cell dry weight and thus constitutes a considerable improvement over the former methods for recovering HBsAg.

11 Claims, No Drawings

METHOD FOR OBTAINING RECOMBINANT HBSAG

This application is a 371 of PCT/EP0/03476, filed Apr. 17, 2000 and claims the benefit of foreign priority under 35 U. S. C. §119 (a)–(d) from German Application 19918619.7, filed Apr. 23, 1999.

The present invention relates to a method for recovering recombinant HBsAg from HBsAg expressing yeast cells.

The destruction of the cell wall of a microorganism—cell disruption—is the first step in recovering intracellular, biologically active proteins. On a production scale, mechanical disruption methods, such as wet milling in ball mills, have turned out to be suited in recent years.

The high-speed agitator ball mills of a closed constructional type have developed from the conventional ball mills used in pigment processing because of the continuously increasing demands made on comminution and dispersion. They consist of a hollow cylinder rotating about a vertical or horizontal axis, which is filled with mixed oxide beads of glass or zirconium up to a filling degree of 80%. The rotational speed can here not be increased in any desired way for increasing impact/pressure crushing because the centrifugal forces compensate the grinding effect. Furthermore, at increased speeds or filling degrees thermal problems arise that might damage the product to be recovered. A continuous grinding material/grinding body separation is carried out with a sieve cartridge, a rotating sieve gap or with a coaxial annular gap integrated into the bearing housing. The grinding material is cooled via a double jacket around the grinding container; the rotating shaft can also be cooled in part. The disruption principle of wet milling consists in transmitting motional energy from the agitator to the grinding body. This is predominantly done by adhesion forces in combination with displacement forces that are due to the assembly and type of agitator elements. The grinding chamber is activated by this and by cohesive forces. The acceleration of the grinding body in radial direction effects the formation of a laminar flow. Depending on the absolute speed and the size of the grinding bodies moved, the differential speed profiles between the grinding body layers effect high shear forces which apart from collision results are mainly responsible for the destruction of the cell wall of the microorganism.

Cells walls can also be broken mechanically by high pressure homogenizers. Such a device consists essentially of a high-pressure piston pump and a homogenizing unit. A homogenization valve will open when the set pressure is reached, the cell suspension being then pressed through the valve unit at a very high speed. The cell suspension is thus heated by about 2.5° C. per 100 bar. After having left the disruption valve unit the cell suspension is cooled by means of a heat exchanger. Thus, in contrast to wet milling, the disruption material is here heated for a short period of time. While passing through the homogenizing unit the cell suspension is subjected to very high turbulence, cavitation and shear forces. The disruption principle of a high pressure homogenizer consists in the sudden reduction of the energy density in the cell suspension within an extremely short period of time, i.e. the high pressure difference and the rapid pressure drop can be regarded as the main factor for the degree of disruption.

Both mechanical disruption methods are used for different microorganisms. The selection of the respective method depends on the type of the microorganism, in particular on its structure. For instance, both cell disintegration methods are tested in Pittroff, M. et al., DECHEMA-Biotechnol. Conf.; (1990), 4, Pt.B, 1055–60 for various microorganisms, such as *Saccharomyces cerevisiae, Micrococcus luteus* and *Escherichia coli,* and the conclusion could be drawn that morphological differences in the microorganism affect the disintegration performance of the two methods.

For instance, Pittroff, M. et al., DECHEMA-Biotechnol. Conf.; (1992, 5, Pt.B, 687–91, and Pittroff, M. et al, Chem. Ing. Techn.; (1992), 64, 10, 950–53 point out that the high-pressure disruption method is preferably carried out for specific microorganisms, such as rod-shaped bacteria. By contrast, the ball milling method is preferably used for cocci having a round structure. The same disintegration degree was observed for both methods in the disruption of yeast cells of the species *Saccgarintces cerevisiae*.

Furthermore, Luther, H. et al., Acta—Biotechnol.; (1992), 12, 4, 281–91, describe a further comparison between ball mills and high pressure homogenizers for purifying proteins from *Saccgarintces cerevisiae* or *Escherichia coli*. It is confirmed that both yeast and bacterial cells can be disrupted using ball mills or high pressure homogenizers. It has been found to be a disadvantage of high pressure homogenizers that slime-forming microorganisms or mechanical contamination very easily lead to occlusions. It is pointed out with respect to yeast cells that the high pressure homogenizer destroys fewer cells. Although this has not been mentioned explicitly, a lower yield from the high pressure homogenizer has to be assumed.

Schütte, H., Biol. Recombinant-Microorg. Anim. Cells; (1991) Oholo 34 Meet., 293–305 also confirm that high pressure homogenizers effect an efficient disruption of yeast and bacterial cells, but are not very suitable for mycelial organisms.

*Saccgarintces cerevisiae* disruption using a high pressure homogenizer was studied in Baldwin, C., Biotechnol. Tech; (1990), 96, 4, 329–34. It was found that the breakage of cells by means of a high pressure homogenizer generally gave low disruption yields (40% in 5 passes). A total disruption of yeast cells in the high pressure homogenizer could only be observed if an enzyme treatment with zymolase from *Oerskovia xanthineolytica* had been performed previously.

As becomes further apparent from the extensive studies that have so far been carried out, the type of the protein to be purified is of decisive importance to the selection of the respective disruption method. Of particular interest is here the cell disruption of hepatitis B surface antigen (HBsAg)-expressing cells.

Choo, K. B. et al., Biochem. Biophys. Res. Commun.; (1985), 131, 1, 160–66 study the use of ball mills for the disruption of *Saccgarintces cerevisiae* cells for the recovery of HBsAg. However, only a low amount of HBsAg could be extracted in particulate form.

Fenton D. M. et al., Abstr. Ann. Med. Am. Soc. Microbiol.; (1984), 84 Meet. 193 describe the release of recombinant HBsAg from *Saccgarintces cerevisiae* by means of cell disruption in a high pressure homogenizer. It is pointed out in this document that the solubilization of HBsAg in an active, i.e. antigenic, form on a large scale poses problems. Sufficient cell breakage and satisfactory protein release were only observed in a high pressure homogenizer after ten passes, and a maximum HBsAg release could only be observed after 15 passes. The authors drew the conclusion that the release of antigenically active HBsAg requires the disruption of subcellular structures.

Hence, up to now it has not been possible with the two disruption methods to provide suitable systems for the optimum production of HBsAg by cell disruption.

It is therefore the object of the present invention to develop a method for recovering a high yield of recombinant HBsAg from recombinant microorganisms.

According to the invention this object is achieved by a method for recovering recombinant HBsAg, wherein recombinant methylotrophic yeast cells which are capable of expressing HBsAg are disrupted using a high pressure homogenizer, and HBsAg is recovered from the cell debris obtained.

Surprisingly enough, it has been found that in the cell disruption of HBsAg-expressing *Hansenula polymorpha* cells in a high pressure homogenizer a considerably higher product yield per g of cell dry weight could be achieved than with the conventional methods, in particular the cell disruption of *Saccharomyces cerevisiae* by means of a high pressure homogenizer or glass bead mills. The method of the invention is thus a considerable improvement over the formerly known methods used for recovering HBsAg from microorganisms.

In the method of the invention, recombinant HBsAg is recovered from recombinant methylotrophic yeast cells which are capable of expressing HBsAg. Preferably, an HBsAg-expressing strain of the species Hansenula is used, particularly preferably *Hansenula polymorpha*. Methylotrophic yeasts of the species Pichia, Candida and Torulopsis can also be used. During fermentation the standard parameters, such as pH, aeration and temperature, are controlled. Glycerol, methanol and glucose, preferably glycerol, are suited as the substrate. The substrate is supplied to the fermenter culture until the yeast cells reach a desired cell density of at least 80, preferably at least 90 $g·l^{-1}$ cell dry weight. After said cell density has been reached, the expression of HBsAg is induced in the yeast culture.

In preferred embodiments the expression of HBsAg in methylotrophic yeast is controlled by a promoter which derives from a gene involved in methanol metabolism. Well-described promoters are the MOX promoter, the DAS and the FMD promoter (Ledeboer, A. M. et al., Nucl. Acids Res. (1985), 13, 9, 3063–3082; Janowics, Z. A. et al., Nucl. Acids Res. (1995), 13, 9, 2043–3062, EP 299 108). To achieve an optimum expression under the control of said promoters, the yeast cells are first grown in a fully synthetic nutrient medium. Methanol is added for induction so that the cell suspension has about 1% of methanol. Detailed information on the culturing of methylotrophic yeasts and the induction conditions for the three above-mentioned promoters can e.g. be found in Gelissen, G. in Murooka/Imanaka (eds.) Recombinant microbes for industrial and agricultural applications, Marcel Dekker, NY 1993, 787–796 and Weydemann, U. et al., Appl. Microbiol. Biotechnol. (1995), 44, 377–385.

Upon completion of the fermentation process the cells are separated from the medium components via tangential flow filtration. A desired cell density is adjusted by suitable dilution with a disruption buffer.

For disruption the yeast cells are preferably used at a cell density of 50 to 150 $g·l^{-1}$ cell dry weight. The exact cell density depends on the respective recombinant methylotrophic yeast cell species. In particular, a cell density of 70 to 120 $g·l^{-1}$ cell dry weight is preferred. If the cell density of the recombinant methylotrophic yeast cells to be used according to the invention is too low, the method becomes time-consuming and uneconomic. At an excessively high cell density of the yeast cells, the disruption becomes more and more inefficient, and the demands on the cooling capacity are increasing.

The high pressure homogenizer used according to the invention is a conventional high-pressure homogenizer, as described in the introduction, which can be used for cell disruption. Particularly preferred is the use of a high pressure homogenizer of the type Nanojet LAB30 PL or a comparable model. During cell disruption the pressure in the homogenizing unit is 1000 to 2000 bar. A pressure of 1200–1600 bar is preferred. Particularly preferred is a pressure of 1500–1600 bar.

The starting temperature of the yeast cells is preferably 2–15° C., particularly preferably 48–8° C. The yeast cells which are normally present in the form of a cell suspension can be cooled under stirring to the desired temperature. The high pressure homogenizer is preferably cooled, so that a low outlet temperature of e.g. 2–15° C., preferably 3–13° C., particularly preferably 5–10° C., is observed at the product outlet.

In the high pressure homogenizer the cells are normally disrupted in several cycles (passes). It has been found that a total of 3 to 8 cycles (passes) are sufficient for an optimum product yield. Preferred are 3 to 6, particularly preferred 4 cycles (passes) for the cell disruption for recovering recombinant HBsAg.

After completion of the cell disrupting process the preparation produced in this way is preferably subjected to further separating and purifying steps. Said additional process steps are conventional methods which effect a further purification and enrichment of recombinant HBsAg in the extract. For instance, one or more of the following separating and purifying steps can be carried out, e.g. in the order indicated:

Precipitation of the cell debris with polyethylene glycol, separation of the PEG supernatant, adsorption on a silica matrix, separation of the silica matrix, desorption of the product from the silica matrix, separation of the supernatant of the silica matrix, ion exchange chromatography, concentration of the ion exchanger pool by ultrafiltration, density gradient separation in cesium chloride, size-exclusion chromatography and sterile filtration (final aqueous bulk).

The following example will explain the invention.

Example 1

Cell Disruption of Hansenula Polymoroha for Recovering HBsAg by High Pressure Disruption 1. High Pressure Homogenizer A device of the following specification was used for the high-pressure disruption method:

| Nanojet Lab30 PL: | |
| --- | --- |
| disruption principle: | high pressure |
| volume flow: | (100 ± 20) ml-min$^1$, not adjustable |
| input pressure of the piston pump: | 4–7 bar |
| pressure of the homogenizing unit: | 1200–1600 bar |
| homogenizing valve: | tungsten carbide |
| cooling: | tubular heat exchanger |
| cell dry weight: | 70 g-l$^1$ |
| seals: | EPDM |
| high pressure seal: | Buna N |
| material: | 1-45-71 steel |

2. Microorganism and Culture Thereof

An HBsAg-expressing *Hansenua polymorpha* strain, e.g. the strain described in Janowicz et al, Yeast, 7:431–443, 1991, is grown in a fully synthetic nutrient medium. During fermentation pH, aeration and temperature are controlled. During fermentation glycerol is intermittently supplied to the fermenter culture in response to the concentration of dissolved oxygen as a substrate up to a cell density of about 90g·l$^{-1}$ cell dry weight. From a cell density of about 90 g·l$^{-1}$ cell dry weight and a fermentation time of about 46 hours the expression of HBsAg is induced in the *Hansenula polymorpha* culture by adding methanol once within 18 to 26 hours. The cell dry weight is determined from a culture aliquot by evaporation on a dry weight balance until constancy of weight. After the final addition the culture is grown for another 2 to 9 hours. Subsequently, the cells are largely freed from fermentation medium components by cross flow filtration. Prior to disruption the cells are buffered. 20 mM phoshate buffer and 2 mM Na$_2$-ethylenediamine tetraacetic acid 2H$_2$O (Triplex Ill) are used for buffering. 75 mg detergent Tween $_2$ 0 per g cell dry weight are fed to the final suspension. For disruption *Hansenula-polymorpha* fermenter culture broths are used at a cell density of about 70 $g \cdot l^{-1}$ cell dry weight.

3. Cell Disruption

The buffered cells are cooled under stirring to 4–8° C. The starting temperature on the disruption device is set to 8±5° C. The cell extract is collected in a separate cooled stirrer vessel.

The volume flow in the high pressure homogenizer is determined by the piston stroke volume and the number of strokes per minute and cannot be adjusted individually. As a rule, disruption is carried out at a flow rate of 100 ml cell suspension per minute. The cells are disrupted in a total of four cycles. After cycle 4 has been terminated, an adjustment to 2 mM final concentration is carried out with 80 mM PMSF stock solution.

After cell disruption the product can be purified by the following separating and purifying steps in the indicated order or in a different order:
precipitation of the cell debris with polyethylene glycol
separation of the PEG supernatant
adsorption on a silica matrix
separation of the silica matrix
desorption of the product from the silica matrix
separation of the supernatant of the silica matrix
ion-exchange chromatography
concentration of the ion exchanger pool by ultrafiltration
density gradient separation in cesium chloride
size-exclusion chromatography
sterile filtration (final aqueous bulk)

To study the efficiency of high pressure disruption, the total protein content is determined by the Lowry method, and the concentration of HBsAg by an immunological method ("ELISA") in the cell extracts.

The Nanojet high-pressure disruption was carried out on a 10-l fermentation scale. To guarantee comparability, the yield of HBsAg is related to the respective cell mass prior to cell disruption.

4. Result 4.1 Testing of the Nanojet High-Pressure Disruption

| Strain: | *Hansenula polymorpha* K3/8-1 |
| --- | --- |
| starting material: | 10-liter fermenter culture RL-98/17 |
| target: | determination of the necessary number of disruption cycles |

| passage | total protein [mg] | total HBsAg (product) [mg] |
| --- | --- | --- |
| NJ-2-1 | 2208 | 118 |
| NJ-2-2 | 3898 | 278 |
| NJ-2-3 | 4968 | 340 |
| NJ-2-4 | 4884 | 440 |
| NJ-2-5 | 4795 | 430 |
| NJ-2-6 | 5088 | 434 |

A significant increase in protein and product (HBsAg) could no longer be detected from the fourth passage onwards. A passage number of four was therefore set for the further tests.

4.2 Disruption Efficiency of Nanojet High-Pressure Disruption for Crude Extract and "Final Aqueous Bulk" (Final Product)

The "final aqueous bulk" is the preparation obtained after the above-mentioned separation and preparation steps have been carried out:

| strain: | *Hansenula polymorpha* K3/8-1 |
| --- | --- |
| starting material: | 10-l fermenter culture NJ-4( ) RL-98/19), NJ-6, -7 |

| Nanojet LAB30PL | mg protein/g cell dry weight | | mg HBsAg/g cell dry weight | |
| --- | --- | --- | --- | --- |
| | crude extract | final aqueous bulk | crude extract | final aqueous bulk |
| Fermentation NJ-4 | 128,2 | 1,98 | 10,8 | 1,77 |
| Fermentation NJ-6 | 100,4 | 1,29 | 7,1 | 1,41 |
| Fermentation NJ-7 | 92,6 | 0,99 | 6,9 | 1,10 |
| Average | 107,1 | 1,42 | 8,3 | 1,43 |

Comparative Example 1

Cell Disruption of *Hansenula polymoroha* for Recovering HBsAa by Wet Milling

1. Glass Bead Homogenizer

Devices of the following specification were used for the wet milling method.

| Fryma Coball Mill MS18: | |
| --- | --- |
| disruption principle: | wet milling |
| rotor diameter: | 192 mm |
| effective grinding volume: | 1200 ml |
| filling with grinding bodies: | 70–80% of the effective grinding volume |
| grinding gap: | 6.50 mm |
| separation gap: | 0.05 mm |
| sieve gap: | 0.20 mm |
| differential gap: | 0.18 mm |
| circumferential speed of rotor: | 14 $m \cdot s^{-1}$ |
| cooling: | double jacket and rotor cooling |
| cell dry weight: | 100–120 g-l-1 |
| volume flow: | 200–300 $ml \cdot min^{-1}$ |
| sealing material: | ethylene propylene |

| Dyno Mill KDL Spezial: | |
| --- | --- |
| disruption principle: | wet milling |
| effective milling chamber volume: | 600 ml |
| stirring disks: | 4,polyurethane |
| filling with grinding bodies: | 80–85% of the effective grinding volume |
| rotational speed: | 6.8 $m \cdot s^{-1}$ |
| coaxial annular gap: | 0.1 mm |
| cooling: | double jacket |
| cell dry weight | 70 $g \cdot l^{-1}$ |
| volume flow: | 100 $ml \cdot min^{-1}$ |
| sealing material: | Viton |

Glass beads with a diameter of 0.45 to 0.55 mm were used for wet milling.

2. Microorganism and Culture Thereof

Use is made of the same materials as in Example 1; however the fermenter culture broths have a cell density of 70 to 120 $g \cdot l^{-1}$ cell dry weight.

3. Cell Disruption

Pretreatment and aftertreatment are carried out as described in Example 1.
Wet milling in the Dyno Mill KDL Spezial The horizontally oriented disruption chamber is continuously fed via a peristaltic pump having a volume flow of 100 $ml \cdot min^{-1}$ cell suspension containing 70 $g \cdot l^{31\ 1}$ cells. At the same time an 80 mM PMSF solution is added for protease inhibition with 1/40 of the cell suspension flow to a separate input port of the disruption chamber under immediate mixing. The cell suspension is disrupted in one cycle.

Wet milling in the Fryma Coball Mill MS18

The cell suspension of the vertically oriented disruption chamber is here also continuously fed by a peristaltic pump. However, the cell density in this instance is 100 to 120 g·l$^{-1}$, the volume flow is set to 200 to 300 ml·min$^{-1}$. In contrast to the Dyno Mill KDL Spezial, the protease inhibitor stock solution (80 mM PMSF) is not added before the ball mill outlet. The cell suspension is disrupted in one cycle. The final concentration of PMSF in the final cell extract is 2 mM.

The disruption tests with the Fryma Coball Mill MS18 were carried out on a 50-l scale. A 10-l fermentation scale was used in wet milling with the Dyno Mill KDL Spezial. To ensure comparability, the yield of HBsAg is related to the respective cell mass prior to cell disruption.

4. Results 4.1 Disruption Efficiency in Dyno Mill Glass-Bead Disruption

| Strain: | *Hansenula polymorpha* K3/8-1 | |
|---|---|---|
| Starting material: | 10-I fermenter culture RL-98/19 | |
| disruption device | process step | mg$_{protein}$/g cell dry weight (Lowry) | mg$_{HBsAg}$/g cell dry weight (ELISA) |
| Dyno Mill KDL | crude extract | 69,4 | 2,35 |

4.2 Disruption Efficiency in Fryma Glass-Bead Disruption up to the Final Product "Final Aqueous Bulk"

| Strain: | *Hansenula polymorpha* K3/8-1 | | | |
|---|---|---|---|---|
| Starting material: | 50-liter fermenter culture RL-98/26, /29,/35 | | | |
| | mg protein/g cell dry weight | | mg HBsAg/g cell dry weight | |
| Fryma Coball Mill MS18 | crude extract | final aqueous bulk | crude extract | final aqueous bulk |
| Fermentation RL-98/26 | 75,7 | 0,56 | 2,85 | 0,53 |
| Fermentation RL-08/29 | 78,5 | 0,53 | 3,00 | n.d. |
| Fermentation RL-98/35 | 92,7 | 0,55 | 2,86 | 0,55 |
| Average | 82,3 | 0,55 | 2,90 | 0,54 |

Example 2

Comparison Between Wet Milling and High Pressure Disruption

1. Disruption Efficiency of Nanojet High-Pressure Disruption and Dyno Mill Glass-Bead Disruption In comparison with cell disruption in the Dyno Mill glass bead mill, a product amount which is four times higher per gram of dry substance is released from an identical starting material. The total protein amount only increases by the factor two at the same time. Consequently, a greater amount of product (HBsAg) is released from the same starting material. The initial product yield increase in the high pressure disruption method is maintained after all subsequent process steps up to the final aqueous bulk, and the product quality corresponds to that of the standard method (wet milling). This could be shown by means of the described combination of Lowry and ELISA.

2. Disruption Efficiency of Nanojet High-Pressure Disruption and Fryma Coball Mill Glass Bead Disruption Viewed over the average of three passes each, a product amount which is 2.9 times higher per gram of cell dry weight is released by Nanojet high-pressure disruption in comparison with glass bead disruption. The higher product amount from cell disruption yields an amount of purified product in the final aqueous bulk that is 2.6 times higher. The quality of the products is for both disruption methods within the same specification, as confirmed by the following analytical certificates.

3. Analytical Results 3.1 High Pressure Disruption

Sample rHBsAg batch no.NJ6 GFC

| Test | Results | RB specification[1] | Remarks |
|---|---|---|---|
| Protein content Lowry | 3,96 mg/ml | | |
| Protein purity SDS-PAGE/ Colloidal Commassie staining | >95% pure | ≧095% | positive |
| Identity Western blot | reactive | reactive with anti-HbsAg antibodies | positive |
| Reactivity AUSZYME | 6,61 mg/ml 1,67 mg/mg protein | >1 mg/mg protein | positive |
| Lipid content Merckotest | 2,43 mg/ml 0,61 mg/mg protein | 0,5–1,8 mg Lipid/ 1,0 mg protein | positive |
| DNA content Threshold | 1221 pg DNA/ml 6,1 pg/20 µg protein | <100 pg/20 µg protein | positive |
| Cesium content HR-ICP-MS[2] | 8,7 ng/ml 43,5 pg/20 µg protein | <10 µg/20 µg protein | positive |
| Carbohydrate content Orcinol | 101 pg/ml 25,5 µg/mg protein | <50 pg/mg protein | positive |
| Endotoxin content LAL[3] | 0,16 EU[4]/ml 0,04 EU/mg protein | <100 EUlmg protein | positive |

[1]Fixed limit values with reference to information furnished by the WHO (World Health Organization) and the European Pharmacopeia
[2]High resolution-inductive coupled plasma - mass spectrometry
[3]Limulus amoebocyte lysate (test method for detecting endotoxin)
[4]Endotoxin units

3.2 Glass Bead Disruption

Sample
  rHBsAg
  batch no. RL98/35 Final Bulk

| Test | Results | RB specification[1] | Remarks |
|---|---|---|---|
| Protein content Lowry | 1,39 mg/ml | 1,0–2,0 mg/ml | positive |
| Protein purity SDS-PAGE/ Colloidal Comassie-staining | >95% pure | >95% | positive |
| Identity Western blot | reactive | reactive with anti-HBsAg antibodies | positive |
| Reactivity AUSZYME | 1,92 mg/ml 1,38 mg/mg protein | >1 mg/mg protein | positive |
| Lipid content Merckotest | 1,13 mg/ml 0,81 mg/mg protein | 0,5–1,8 mg lipid/ 1,0 mg protein | positive |
| DNA content threshold | 56,4 pg DNA/ml 0,8 pg/20 μg protein | <100 pg/20 μg protein | positive |
| Cesium content HR-ICP-MS[2] | 8,2 ng/ml 118 pg/20 μg protein | <10 μg/20 μg protein | positive |
| carbohydrate content Orcinol | 35,8 μg/ml 26 μg/mg protein | <50 μg/mg protein | positive |
| Endotoxin content LAL[3] | 0,75 EU[4]/ml 0,54 EU/mg protein | <100 EU/mg protein | positive |

[1]Fixed limit values with reference to information furnished by the WHO (World Health Organization) and the European Pharmacopeia
[2]High resolution-inductive coupled plasma - mass spectrometry
[3]Limutus amoebocyte lysate (test method for detecting endotoxin)
[4]endotoxin units

4. Conclusion

The above analyses furnish proof that in contrast to the assumption made in the prior art high pressure disruption is of considerable advantage to yeast cells, at least for yeast cells of the methylotrophic type. With high pressure disruption the yield can be increased by 2.5 to 4 times.

What is claimed is:

1. A method for recovering recombinant Hepatitis B surface Antigen ("HBsAg"), wherein recombinant methylotrophic yeast cells which are capable of expressing recombinant HBsAg are disrupted using a high pressure homogenizer, and recombinant HBsAg is recovered from the cell debris obtained.

2. The method according to claim 1, characterized in that the recombinant methylotrophic yeast cell is a yeast cell of the species Hansenula.

3. The method according to claim 1 or 2, characterized in that the recombinant methylotrophic yeast cells are used for disruption at a cell density of 50–150 g·l$^{-1}$ cell dry weight.

4. The method according to claim 1 or 2, characterized in that the recombinant methylotrophic yeast cells are disrupted at a pressure of 1000 to 2000 bar in the homogenizing unit of the high pressure homogenizer.

5. The method according to claim 1 or 2, characterized in that the temperature at the product outlet is 2° C. to 15° C.

6. The method according to claim 1 or 2, characterized in that the recombinant methylotrophic yeast cells are disrupted in 3 to 6 cycles (passages).

7. The method according to claim 3, characterized in that the recombinant methylotrophic yeast cells are disrupted at a pressure of 1000 to 2000 bar in the homogenizing unit of the high pressure homogenizer.

8. The method according to claim 3, characterized in that the temperature at the product outlet is 2° C. to 15° C.

9. The method according to claim 3, characterized in that the recombinant methylotrophic yeast cells are disrupted in 3 to 6 cycles (passages).

10. The method according to claim 4, characterized in that the recombinant methylotrophic yeast cells are disrupted in 3 to 6 cycles (passages).

11. The method according to claim 5, characterized in that the recombinant methylotrophic yeast cells are disrupted in 3 to 6 cycles (passages).

* * * * *